United States Patent
Muehlsteff et al.

(10) Patent No.: US 12,414,716 B2
(45) Date of Patent: Sep. 16, 2025

(54) PHOTOPLETHYSMOGRAPHY PULSE OXIMETER FOR CARDIOPULMONARY RESUSCITATION

(71) Applicant: KONINKLIJKE PHILIPS N.V., Eindhoven (NL)

(72) Inventors: Jens Muehlsteff, Aachen (DE); Ralph Wilhelm Christianus Gemma Rosa Wijshoff, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1203 days.

(21) Appl. No.: 17/260,059

(22) PCT Filed: Jul. 12, 2019

(86) PCT No.: PCT/EP2019/068831
§ 371 (c)(1),
(2) Date: Jan. 13, 2021

(87) PCT Pub. No.: WO2020/011982
PCT Pub. Date: Jan. 16, 2020

(65) Prior Publication Data
US 2021/0282670 A1    Sep. 16, 2021

Related U.S. Application Data

(60) Provisional application No. 62/697,561, filed on Jul. 13, 2018.

(51) Int. Cl.
| | | |
|---|---|---|
| A61B 5/1455 | (2006.01) | |
| A61B 5/00 | (2006.01) | |
| A61B 5/024 | (2006.01) | |

(52) U.S. Cl.
CPC ........ *A61B 5/1455* (2013.01); *A61B 5/02416* (2013.01); *A61B 5/742* (2013.01); *A61B 2505/01* (2013.01)

(58) Field of Classification Search
CPC ... A61B 5/1455; A61B 5/02416; A61B 5/742; A61B 2505/01
See application file for complete search history.

(56) References Cited

U.S. PATENT DOCUMENTS

2004/0039269 A1 *  2/2004  Ward ............... A61B 5/0086
                                                    600/312
2004/0267324 A1    12/2004 Boucher et al.
(Continued)

FOREIGN PATENT DOCUMENTS

WO    2011086520 A1    7/2011

OTHER PUBLICATIONS

Spittal, M.J.. "Evaluation of pulse oximetry during cardiopulmonary resuscitation". Anaesthesia, vol. 48, No. 8, (Aug. 1, 1993), pp. 701-703.
(Continued)

*Primary Examiner* — Alex M Valvis
*Assistant Examiner* — Jonathan M Haney

(57) ABSTRACT

A PPG pulse oximeter employing a dual PPG probe including a central PPG sensor and a peripheral PPG sensor connectable in a circuit configuration with a pulse oximeter monitor. In operation, the pulse oximeter monitor controls synchronous generations of a central PPG signal by the central PPG sensor and of a peripheral PPG signal by the peripheral PPG sensor, and also control a CPR pulse detection via the dual PPG probe including a detection of a presence of a spontaneous pulse of the central PPG signal and a detection of a presence of a spontaneous pulse of the peripheral PPG signal.

15 Claims, 8 Drawing Sheets

(56) References Cited

U.S. PATENT DOCUMENTS

| | | | |
|---|---|---|---|
| 2010/0081892 | A1 | 4/2010 | Addison et al. |
| 2013/0324808 | A1 | 12/2013 | Abdul-Hafiz et al. |
| 2015/0099951 | A1 | 4/2015 | Dejong et al. |
| 2015/0380875 | A1 | 12/2015 | Coverston et al. |
| 2016/0206504 | A1* | 7/2016 | Giarracco .......... A61B 5/14551 |
| 2016/0374623 | A1 | 12/2016 | Muehlsteff et al. |
| 2017/0027488 | A1* | 2/2017 | Enenkel ................ A61B 5/443 |

OTHER PUBLICATIONS

International Search Report for PCT/EP2019/068831 dated Jul. 12, 2019.

Berg, R.A. et al., "Adverse Hemodynamic Effects of Interrupting Chest Compressions for Rescue Breathing During Cardiopulmonary Resuscitation for Ventricular Fibrillation Cardiac Arrest". Circulation, Journal of the American Heart Association. 201;104:2465-2470.

Christenson, J. et al., "Chest Compression Fraction Determines Survival in Patients with Out-of-Hospital Ventricular Fibrillation". Circulation, Journal of the American Heart Association. 2009;120:1241-1247.

Link, M.S. et al., "Part 7: Adult Advanced Cardiovascular Life Support—2015 American Heart Association Guidelines Update for Cardiopulmonary Resuscitation and Emergency Cardiovascular Care". Circulation, Journal of the American Heart Association. 2015;132[suppl 2]:S444-S464.

Cummingham, L.M. et al., "Cardiopulmnary resuscitation for cardiac arrest: the importance of uninterrupted chest compressions in cardiac arrest resuscitation". American Journal of Emergency Medicine (2012) 30, 1630-1638.

Eberle, B. et al., "Checking the carotid pulse check: diagnostic accuracy of first responders in patients with and without a pulse". Resuscitation 33 (1996) 107-116.

Hubner, P. et al., "Pulse appearance in photoplethysmography signals obtained from finger, nose and ear during extracorporeal life support". Abstracts/Resuscitation 96S(2015) 43-157.

Muehlsteff, J. et al., "Continuous Cuff-less Blood Pressure Monitoring based on the Pulse Arrival Time Approach: The Impact of Posture". Philips Research Europe, 2008.

Moule, P. "Checking the carotid pulse: diagnostic accuracy in students of the healthcare professions". Resuscitation 44 (2000) 195-201.

Ochoa, F. Javier et al., "Competence of health professionals to check the carotid pulse". Resuscitation 37 (1998) 173-175.

Payne, R.A. et al., "Pulse transit time measured from the ECG: an unreliable marker of beat-to-beat blood pressure". J Appl Physiol 100: 136-141, 2006.

Wijshoff, R. et al., "Detection of a spontaneous pulse in photoplethysmograms during automated cardiopulmonary resuscitation in a porcine model". Resuscitation 84 (2013) 1625-1632.

Soar, J. et al., "EUropean Resuscitation Council Guidelines for Resuscitatin 2015 Section 3. Adult advanced life support". Resuscitation 95 (2015) 100-147.

Tibballs, J. et al., "Reliability of pulse palpation by healthcare personnel to diagnose paediatric cardiac arrest". Resuscitation 80 (2009) 61-64.

Wijshoff, R. et al., "Photoplethysmography-Based Algorithm for Detection of Cardiogenic Output During Cardiopulmonary Resuscitation". IEEE Transaction on Biomedical Engineering, vol. 62, No. 3, Mar. 2015.

Wik, L. et al., "Quality of Cardiopulmonary Resuscitation During Out-of-Hospital Cardiac Arrest". JAMA, Jan. 19, 2005—vol. 293, No. 3, pp. 299-304.

* cited by examiner

PHOTOPLETHYSMOGRAPHY PULSE OXIMETER FOR CARDIOPULMONARY RESUSCITATION

This application is a national stage application under 35 U.S.C. § 371 of International Application No. PCT/EP2019/068831 filed on Jul. 12, 2019 and published in the English language on Jan. 16, 2020 as International Publication No. WO2020/011982, which claims priority to U.S. Patent Application No. 62/697,561 filed on Jul. 13, 2018, the entire disclosures of which are incorporated herein by reference.

FIELD OF THE INVENTION

The present disclosure relates generally to photoplethysmography for detecting volumetric changes in a peripheral circulation of blood. The present disclosure specifically relates to an application of photoplethysmography to cardiopulmonary resuscitation.

BACKGROUND OF THE INVENTION

Cardiopulmonary resuscitation (CPR) is an emergency procedure for a person suffering from a cardiac arrest whereby a goal of CPR is to achieve return of spontaneous circulation (ROSC). During CPR, chest compressions are delivered to artificially generate circulation of blood, and ventilations are given to supply blood with oxygen. When ROSC has been achieved, the heart of the cardiac arrested person has resumed beating and generates a spontaneous circulation which is life-sustaining. CPR may therefore be stopped after achieving ROSC.

Determining whether the cardiac arrested person has achieved ROSC involves checking whether the person has a spontaneous circulatory pulse, i.e., whether the heart is beating and generating output. Currently in the art of the present disclosure, pulse checks are typically performed by manual palpation. However, manual palpation is known to be unreliable and time-consuming, and requires interruption of the chest compressions. Manual palpation therefore may take significantly longer than the ten (10) seconds recommended by the CPR guidelines for ROSC assessment, especially when a spontaneous pulse is absent. As a result, manual palpation may lead to long interruptions in the chest compressions, which reduces the compression-generated blood flow and may thereby negatively impact CPR outcome.

Pulse detection may be supported by using photoplethysmography (PPG), which is a readily available, non-invasive and easy-to-use optical technology currently widely applied in pulse oximetry. More particularly, pre-clinical results in the art of the present disclosure support the feasibility of PPG-based pulse detection during CPR.

SUMMARY OF THE INVENTION

In accordance with exemplary embodiments of the present disclosure, the inventions of the present disclosure are derived from a recognition that, when a heart of a cardiac arrested person resumes beating, a spontaneous pulse of the person may be observed directly in a PPG signal measured at a central location of the person (e.g., nose, ear or forehead), and the spontaneous pulse of the person may be subsequently observed in a PPG signal measured at a peripheral location of the person (e.g., finger or toe) with a delay of about sixty (60) seconds. As such, the inventions of the present disclosure premised in view of a central PPG signal being better suited to an early detection of a presence of a spontaneous pulse of the person and further in view of a peripheral PPG signal providing a qualitative measure of the level of circulation of the person (i.e., when a spontaneous pulse of the person is observed peripherally, the inventions of the present disclosure indicate that some minimum level of circulation has been achieved by that person).

More particularly, the inventions of the present disclosure provide devices, controls and methods incorporating two (2) PPG sensors to support pulse detection during CPR. One PPG sensor is placed centrally on a cardiac arrested person to obtain an early indication of presence of a spontaneous pulse, and the other PPG sensor is placed peripherally on the person to obtain a qualitative measure of the level of circulation of the person. Consequently, the central PPG measurement may advantageously provide clinical decision support regarding administration of medication during the CPR, and the peripheral PPG measurement may advantageously provide clinical decision support regarding when to stop chest compressions and further assess for a potential ROSC.

One embodiment of the inventions of the present disclosure is a PPG pulse oximeter comprising a dual PPG probe including a central PPG sensor and a peripheral PPG sensor. The PPG pulse oximeter further comprises a pulse oximeter monitor connectable to the central PPG sensor and the peripheral PPG sensor in a circuit configuration to (1) control synchronous generations of a central PPG signal by the central PPG sensor and of a peripheral PPG signal by the peripheral PPG sensor and (2) also control a CPR pulse detection by the dual PPG probe including a detection of a presence of a spontaneous pulse of the central PPG signal and a detection of a presence of a spontaneous pulse of the peripheral PPG signal.

A second embodiment of the inventions of the present disclosure is a PPG pulse monitoring method. The method involves (1) identifying, by a pulse oximeter monitor, a connection of the pulse oximeter monitor to a dual PPG probe in a circuit configuration including a central PPG sensor and a peripheral PPG sensor, (2) controlling, by the pulse oximeter monitor, synchronous generations of a central PPG signal by the central PPG sensor and of the peripheral PPG signal by the peripheral PPG sensor, and (3) controlling, by the pulse oximeter monitor, a CPR pulse detection by the dual PPG probe including detecting a presence of a spontaneous pulse of the central PPG signal and detecting a presence of a spontaneous pulse of the peripheral PPG signal.

For purposes of describing and claiming the inventions of the present disclosure, the term "pulse oximeter" broadly encompasses all devices, known prior to and subsequent to the present disclosure, for monitoring an oxygen saturation ($SO_2$ or $SpO_2$) of a person and optionally monitoring a pulse rate of the person. Examples of a "pulse oximeter" include, but are not limited to Philips FAST SpO2 as available for the Philips IntelliVue series.

Also for purposes of describing and claiming the inventions of the present disclosure, (1) the term "PPG pulse oximeter" broadly encompasses all pulse oximeters incorporating inventive principles of the present disclosure as exemplary described herein, and the term "PPG pulse monitoring method" broadly encompasses all pulse oximetry based methods that incorporate the inventive principles of the present disclosure as exemplary described herein;

(2) terms of the art including, but not limited to, "CPR", "PPG", "probe", "sensor", "monitor", "light emitter", "light emitting diode", "light detector", "photodetector", "optical fiber", "connector", "socket" and "microcontroller" are to be interpreted as understood in the art of the present disclosure and as exemplary described herein;

(3) the descriptive labeling of the terms "probe", "sensor", "light", "light emitter", "light emitting diode", "light detector" and "photodetector" as either "central" or "peripheral" facilitates a distinction between such terms as described and claimed herein without specifying or implying any additional limitation to the terms;

(4) the term "application module" broadly encompasses a component of a microcontroller including an electronic circuit and/or an executable program (e.g., executable software and/or firmware stored on non-transitory computer readable medium(s)) for executing a specific application. Any descriptive labeling of an application module herein (e.g., a "pulse width modulator" module, "ROSC detector" module and a "ROSC indicator") serves to identify a particular application module as described and claimed herein without specifying or implying any additional limitation to the term "application module"; and (5) the term "signal" broadly encompasses all forms of a detectable physical quantity or impulse (e.g., voltage, current, or magnetic field strength) as understood in the art of the present disclosure and as exemplary described herein for communicating information in support of applying various inventive principles of the present disclosure as subsequently described herein. Any descriptive labeling for the term "signal" herein facilitates a distinction between signals as described and claimed herein without specifying or implying any additional limitation to the term "signal".

The foregoing embodiments and other embodiments of the inventions of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

Figure 1A:
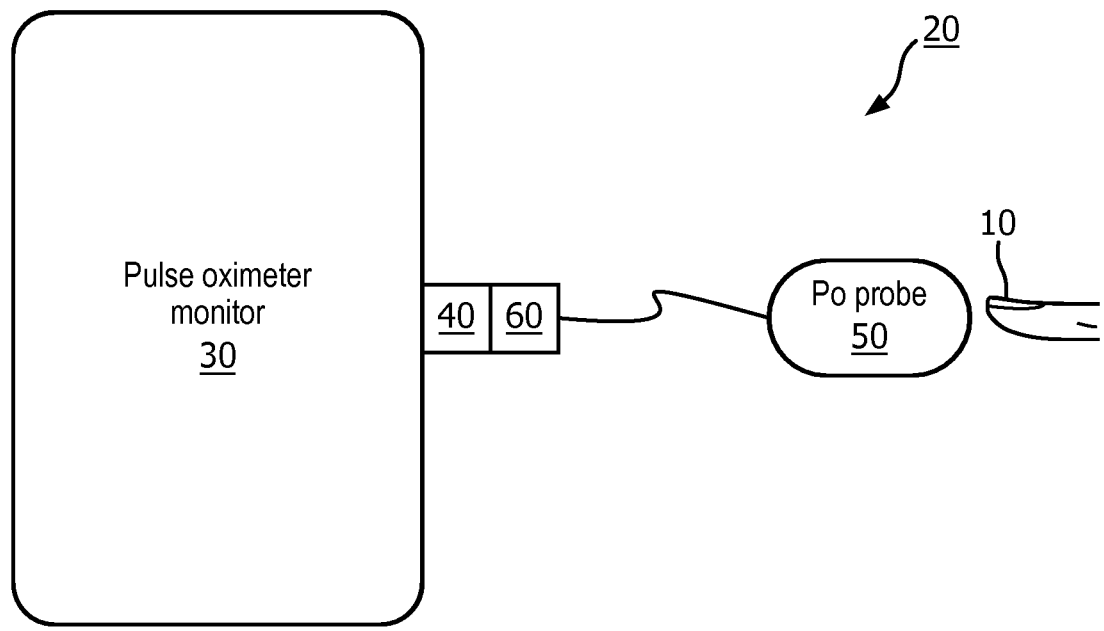
FIGS. 1A and 1B illustrates an exemplary embodiment of pulse oximeter as known in the art of the present disclosure.
Figure 1B:
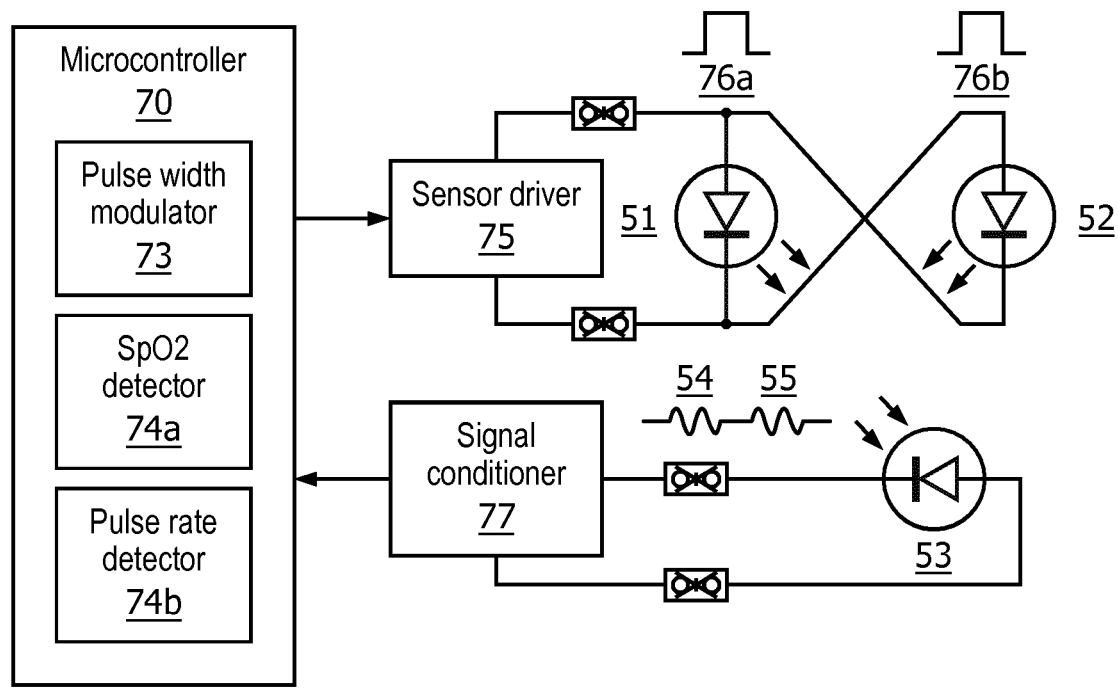

Referring to FIGS. 1A and 1B, a pulse oximeter 20 as known in the art of the present disclosure employs pulse oximeter monitor 30 and a pulse oximeter probe 50 having a connector 60 for plugging into a socket 40 of pulse oximeter monitor 30 to thereby couple a light emitter 51 (e.g., an infra-red light emitting diode) and a light emitter 52 (e.g., a red light-emitting diode) of an SpO2 sensor of pulse oximeter probe 50 in an anti-parallel configuration to a sensor driver 75 of pulse oximeter monitor 30, and for coupling a light detector 53 (e.g., a photodetector) of the SpO2 sensor of pulse oximeter probe 50 to a signal conditioner 77.

In operation, upon a mounting of pulse oximeter probe 50 unto a peripheral location of a person (e.g., a finger 10 as shown), microcontroller 70 executes a pulse width modulator 73 to control a synchronized emission of light by light emitter 51 and light emitter 52 via respective pulses 76a and 76b applied by sensor driver 75 to light emitter 51 and light emitter 52 as known in the art of the disclosure. In practice, pulse 76a and pulse 76b generate optical pulses of different wavelengths, via light emitter 51 and light emitter 52, respectively.

Light emitter 51, light emitter 52 and light detector 53 are optically coupled within pulse oximeter probe 50 whereby light detector 53 will detect light passing through the peripheral location of a person (e.g., finger 10 as shown) to thereby produce a first wavelength detection signal 54 and a second wavelength detection signal 55 as known in art of the present disclosure. Upon being conditioned by signal conditioner 77, microcontroller 70 executes an SpO2 detector 74a to thereby monitor an oxygen saturation of a person as known in the art of the present disclosure, and further executes a pulse rate detector 74b to thereby monitor a pulse rate of the person as known in the art of the present disclosure. Microcontroller 70 employs additional modules (not shown) for displaying and communicating a status of the monitored oxygen saturation of the person and a status of the pulse rate of the person.

To improve upon the prior art of FIGS. 1A and 1B, as will be further described in the present disclosure, embodiments of the inventions of the present disclosure incorporate two (2) single wavelength PPG sensors (e.g., red, near-infrared or green light emitting diodes) using the dual-wavelength pulse oximetry socket 40 (FIG. 1) of known pulse oximeter. This allows for the development of a dedicated CPR dual-PPG-based pulse detection probe which is compatible with the current sockets of pulse oximeters (e.g., socket 40 of pulse oximeter 20).

Figure 2A:
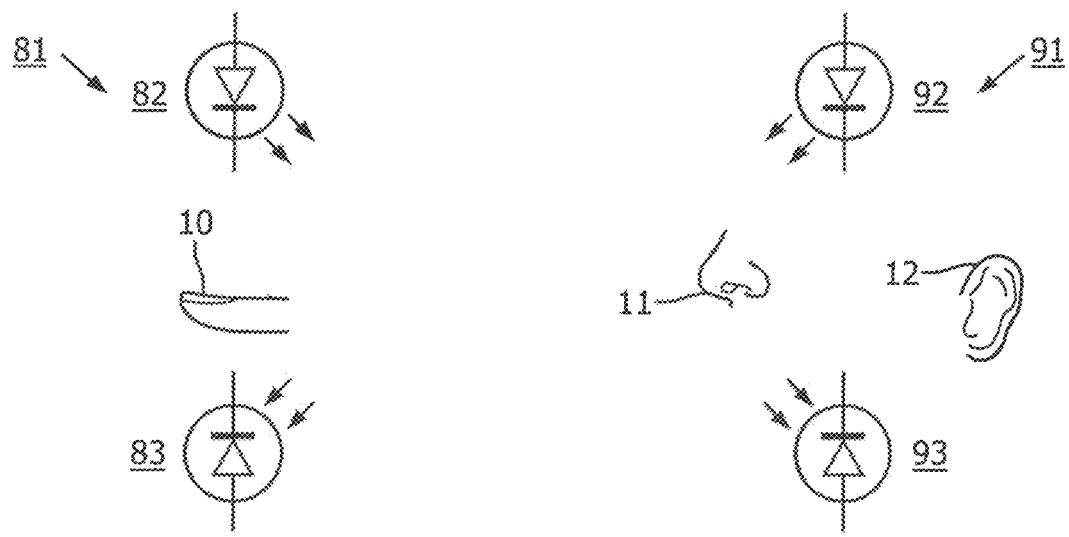
FIGS. 2A and 2B illustrates exemplary embodiments of a PPG sensor pair in accordance with the inventive principles of the present disclosure.
Figure 2B:
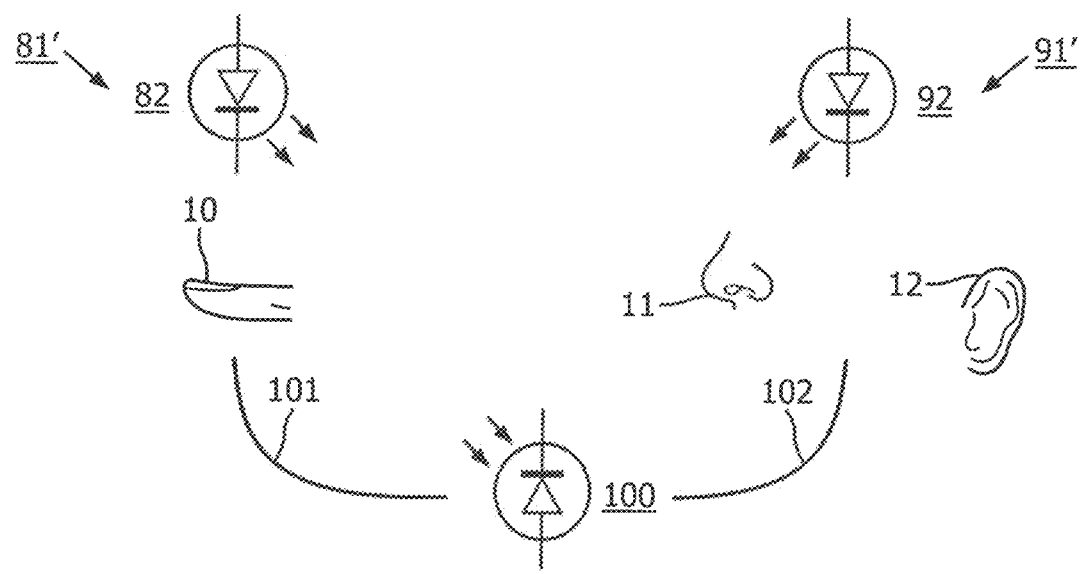
Figure 3:
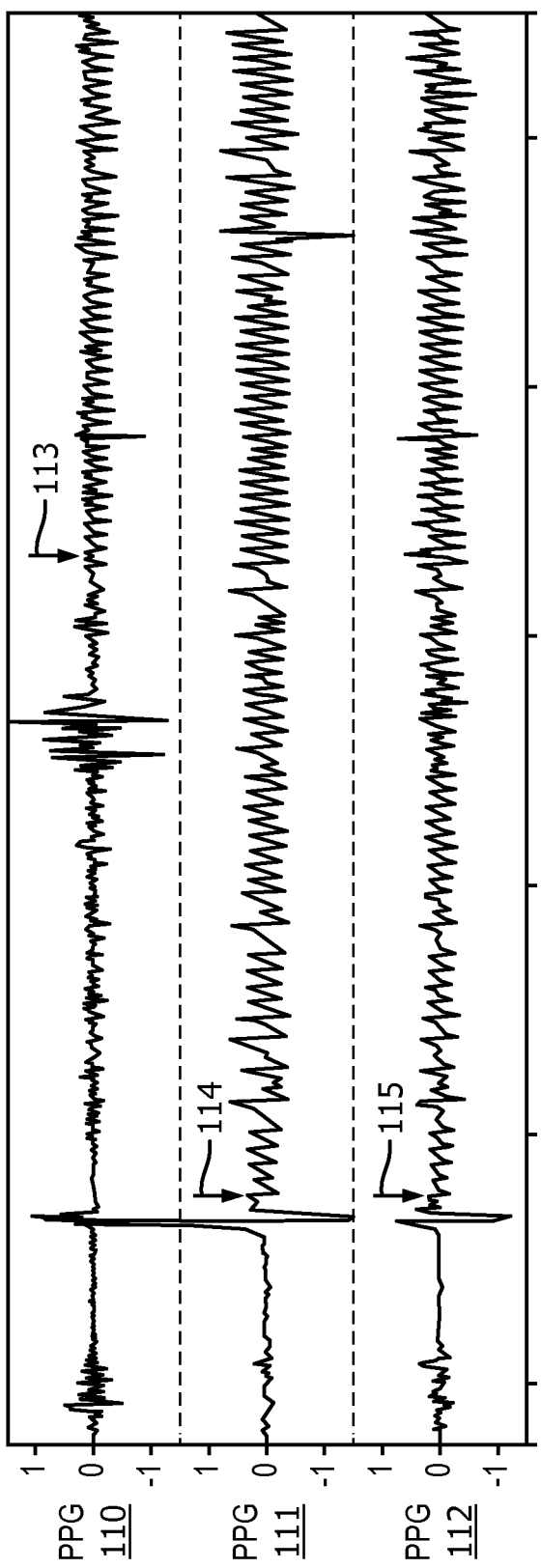
FIG. 3 illustrates exemplary PPG signals in accordance with the inventive principles of the present disclosure.

To facilitate an understanding of the present disclosure, the following description of FIGS. 2 and 3 teaches inventive principles of PPG sensors in accordance with the inventive principles of the present disclosure. From the description of FIG. 1, those having ordinary skill in the art of the present disclosure will appreciate how to apply the inventive principles of the present disclosure for making and using numerous and various embodiments of PPG sensors of the present disclosure.

Referring to FIG. 2A, the inventions of the present disclosure provide for a peripheral PPG sensor 81 employing an optical coupling of a light emitter 82 (e.g., red, near-infrared or green light emitting diode) and a light detector 83 (e.g., a photodiode) whereby light emitted by light emitter 82 through a peripheral location of a person (e.g., finger 10 as shown) is detected by light detector 83. The inventions of the present disclosure further provide for a central PPG sensor 91 employing an optical coupling of a light emitter 92 (e.g., red, near-infrared, or green light emitting diode) and a light detector 93 (e.g., a photodiode) whereby light emitted by light emitter 92 through a central location of a person (e.g., a nose 11 or an ear 12 as shown, or a forehead) is detected by light detector 93.

FIG. 2B illustrates an alternate embodiment of a peripheral PPG sensor 81' and a central PPG sensor 91' sharing a common light detector 100 (e.g., a photodetector) that is optically coupled via an optical fiber 101 to light emitter 82 and optically coupled via an optical fiber 102 to light emitter 92.

FIG. 3 illustrates an exemplary peripheral PPG signal 110 obtained by peripheral PPG sensor 81/81' from finger 10, and central PPG signals 111 and 112 obtained by central PPG sensor 91/91' from a nasal septum of nose 11 and an ear pinna of ear 12. FIG. 3 shows that when the heart of the patient resumes beating, a spontaneous pulse 114 and 115 respectively may be observed directly in the PPG signals 111 and 112 measured centrally at the nose 11 and the ear 12, but with a delay of about sixty (60) seconds for a spontaneous pulse 113 in the peripheral PPG signal 110 measured peripherally at the finger 10. The inventions of the present disclosure are premised on central PPG signals 111 and 112 being better suited to early detect presence of a spontaneous pulse during CPR and peripheral PPG signal 110 providing a more qualitative measure of the level of circulation.

To further facilitate an understanding of the present disclosure, the following description of FIGS. 4-6 teaches inventive principles of PPG pulse oximeters in accordance with the inventive principles of the present disclosure. From the description of FIG. 1, those having ordinary skill in the art of the present disclosure will appreciate how to apply the inventive principles of the present disclosure for making and using numerous and various embodiments of PPG pulse oximeters of the present disclosure.

Figure 4A:
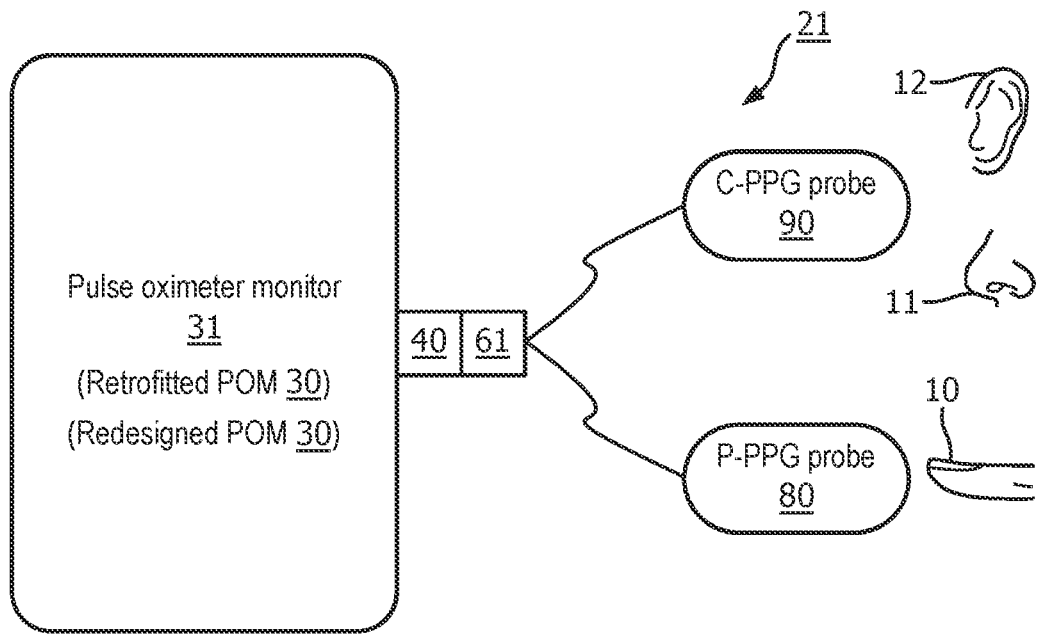
FIGS. 4A and 4B illustrates a first exemplary embodiment of PPG pulse oximeter in accordance with the inventive principles of the present disclosure.
Figure 4B:
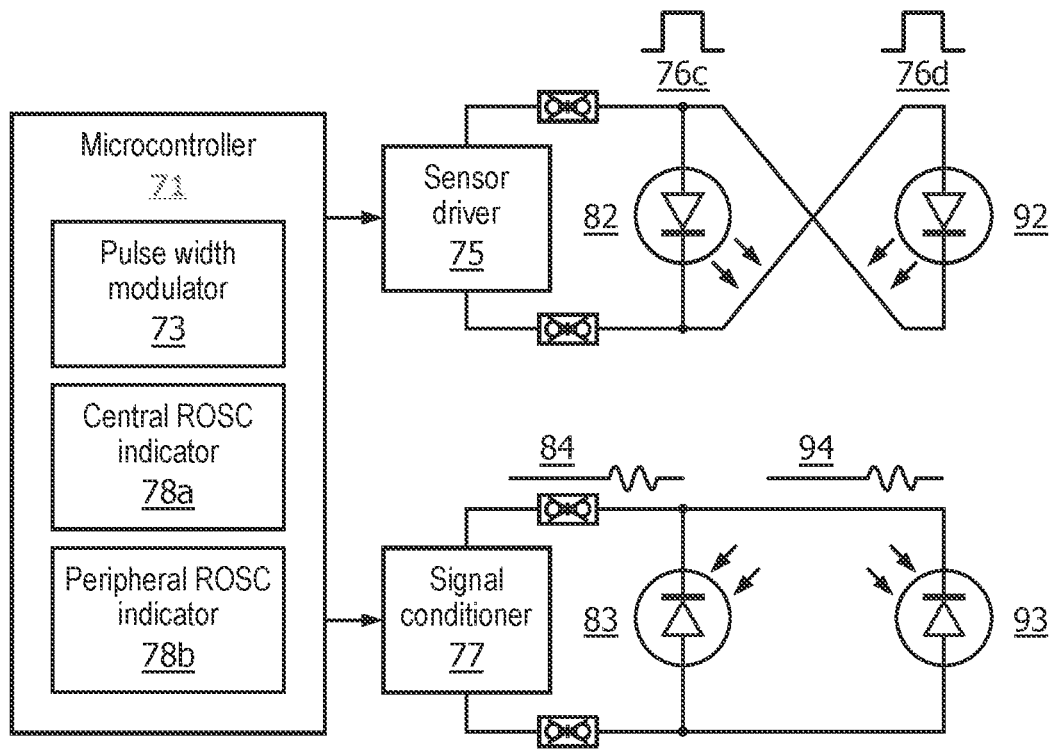

Referring to FIGS. 4A and 4B, a PPG pulse oximeter 21 of the present disclosure employs a pulse oximeter monitor 31 and a dual PPG probe including a peripheral PPG probe 80 and a central PPG probe 90. Pulse oximeter monitor 31 represents a retrofit or a redesign of pulse oximeter 30 (FIG. 1A) whereby a connector 61 of the dual PPG probe is pin-compatible with socket 40 of pulse oximeter monitor 31 and further whereby a microcontroller 71 includes a central ROSC indicator 78a and a peripheral ROSC indicator 78b in addition to or in replacement of SpO2 detector 74a (FIG. 1B) and pulse rate detector 74b (FIG. 1B). More particular to the retrofit or the redesign of pulse oximeter 30, in practice, the compatibility of connector 61 of dual PPG probe 80/90 with socket 40 of pulse oximeter monitor 30 (FIG. 1) enables the hardware of pulse oximeter monitor 31 to be identical to the hardware of pulse oximeter monitor 30 with the addition of firmware implementing central ROSC indicator 78a and peripheral ROSC indicator 78b. Further in practice, for PPG pulse oximeters of the present disclosure incorporating firmware implementing SpO2 detector 74a, pulse rate detector 74b, central ROSC indicator 78a and peripheral ROSC indicator 78b, such PPG pulse oximeters will be capable of differentiating a connection of connector 60 of pulse oximeter probe 50 (FIG. 1A) to socket 40 of pulse oximeter monitor 31 and a connection of connector 61 of dual PPG probe 80/90 to socket 40 of pulse oximeter monitor 31 as will be further described in the present disclosure.

Peripheral PPG probe 80 includes peripheral PPG sensor 81 (FIG. 2A) and central PPG probe 90 includes central PPG sensor 91 (FIG. 2A).

Prior to operation, connector 61 is plugged into a socket 40 to thereby couple a light emitter 82 (e.g., a red, near-infrared or green emitting diode) and a light emitter 92 (e.g., a red, near-infrared or green light-emitting diode) in an anti-parallel configuration to sensor driver 75 of pulse oximeter monitor 31, and for coupling light detector 83 (e.g., a photodetector) and light detector 93 (e.g., a photodetector) in a parallel configuration to signal conditioner 77.

In operation, upon a mounting of peripheral PPG probe 80 unto a peripheral location of a person (e.g., finger 10 as shown) and a mounting of central PPG probe 90 unto a central location of the person (e.g., nose 11 or ear 12 as shown, or a forehead), microcontroller 71 executes pulse width modulator 73 to control synchronized emission of light by light emitter 82 and light emitter 92 via respective pulses 76c and 76d applied by sensor driver 75 to light emitter 82 and light emitter 92 as known in the art of the disclosure. In practice, pulse 76c and pulse 76d may generate optical pulses of the same wavelength, via light emitter 82 and light emitter 92, respectively.

Light emitter 92 and light detector 93 are optically coupled within central PPG probe 90 whereby light detector 93 will detect light passing through the central location of the person (e.g., nose 11 or ear 12 as shown, or a forehead) to thereby produce central PPG signal 94 indicative of a volumetric change in a central circulation of the person. Upon central PPG signal 94 being conditioned by signal conditioner 77, microcontroller 71 executes a central ROSC indicator 78a to indicate an early detection of a beating heart, which may support decision making regarding medication.

Similarly, light emitter 82 and light detector 83 are optically coupled within peripheral PPG probe 80 whereby light detector 83 will detect light passing through the peripheral location of the person (e.g., finger 10 as shown) to thereby produce peripheral PPG signal 84 indicative of a volumetric change in a peripheral circulation of the person. Upon peripheral PPG signal 84 being conditioned by signal conditioner 77, microcontroller 71 executes a peripheral ROSC indicator 78b to provide a qualitative indication of the level of the spontaneous circulation thus providing decision support in when to stop CPR and further assess a potential return of spontaneous circulation (ROSC).

Microcontroller 71 employs additional modules (not shown) for displaying and communicating a status of any pulse detection during, preceding and/or succeeding CPR of the person.

Figure 5A:
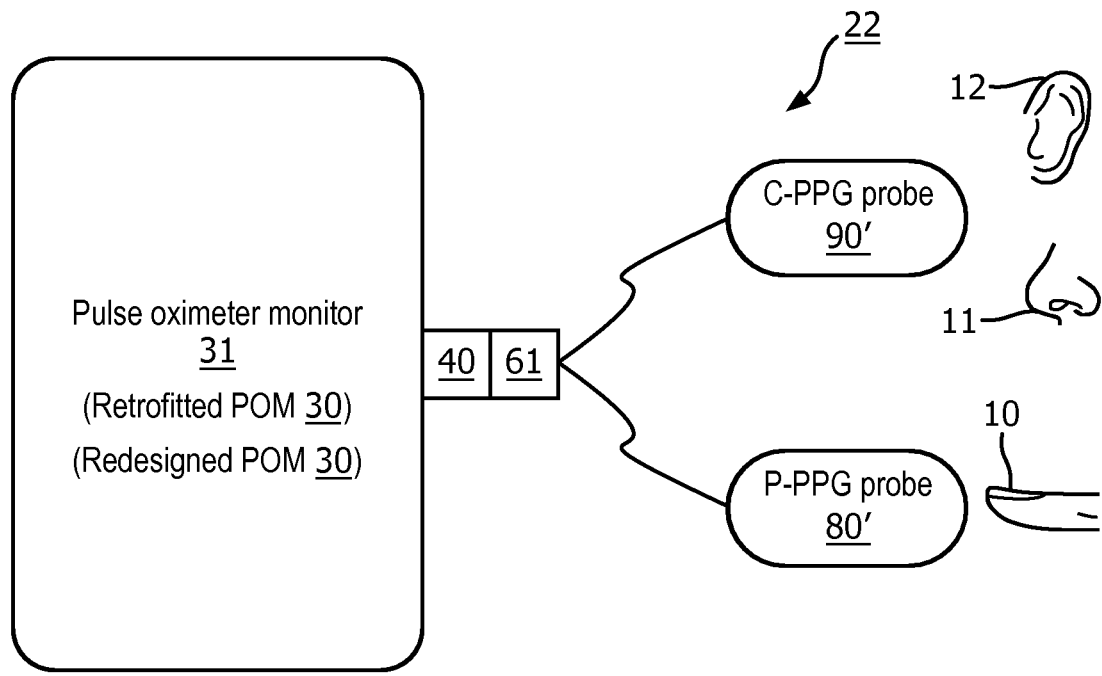
FIGS. 5A and 5B illustrates a second exemplary embodiment of PPG pulse oximeter in accordance with the inventive principles of the present disclosure.
Figure 5B:
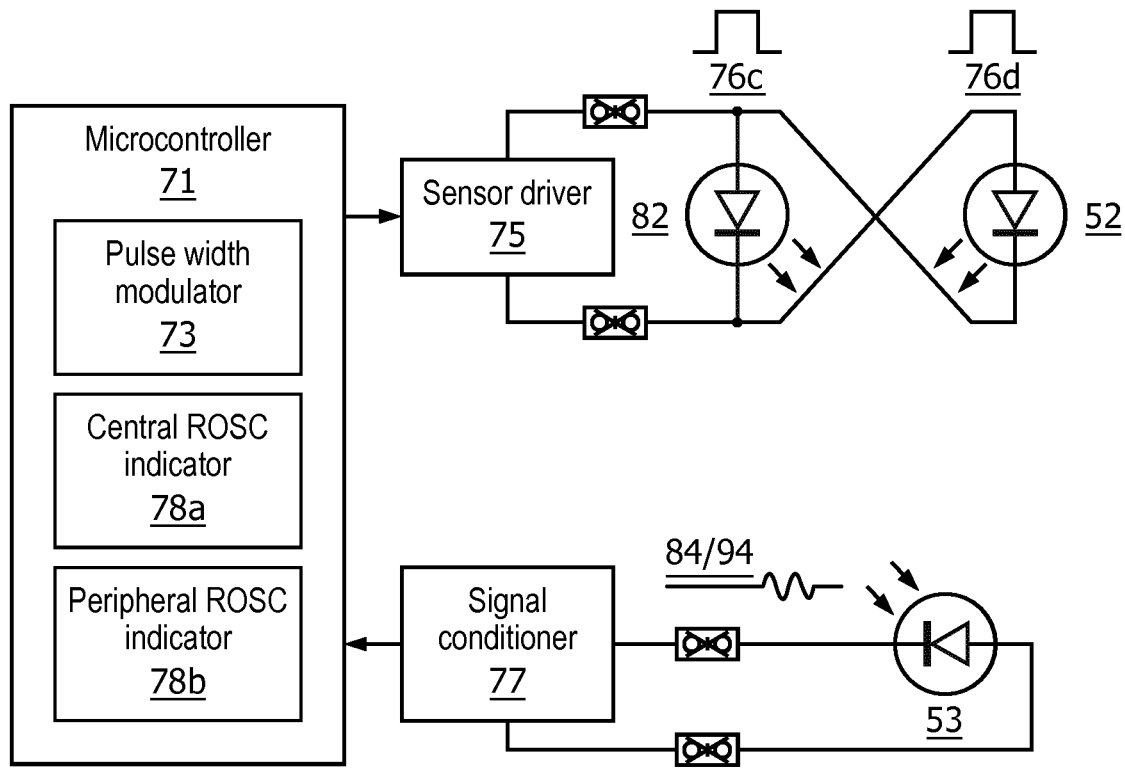

Referring to FIGS. 5A and 5B, a PPG pulse oximeter 22 of the present disclosure employs pulse oximeter monitor 31 and a dual PPG probe alternatively including a peripheral PPG probe 80' and a central PPG probe 90' as shown in FIG. 2B.

Figure 6A:
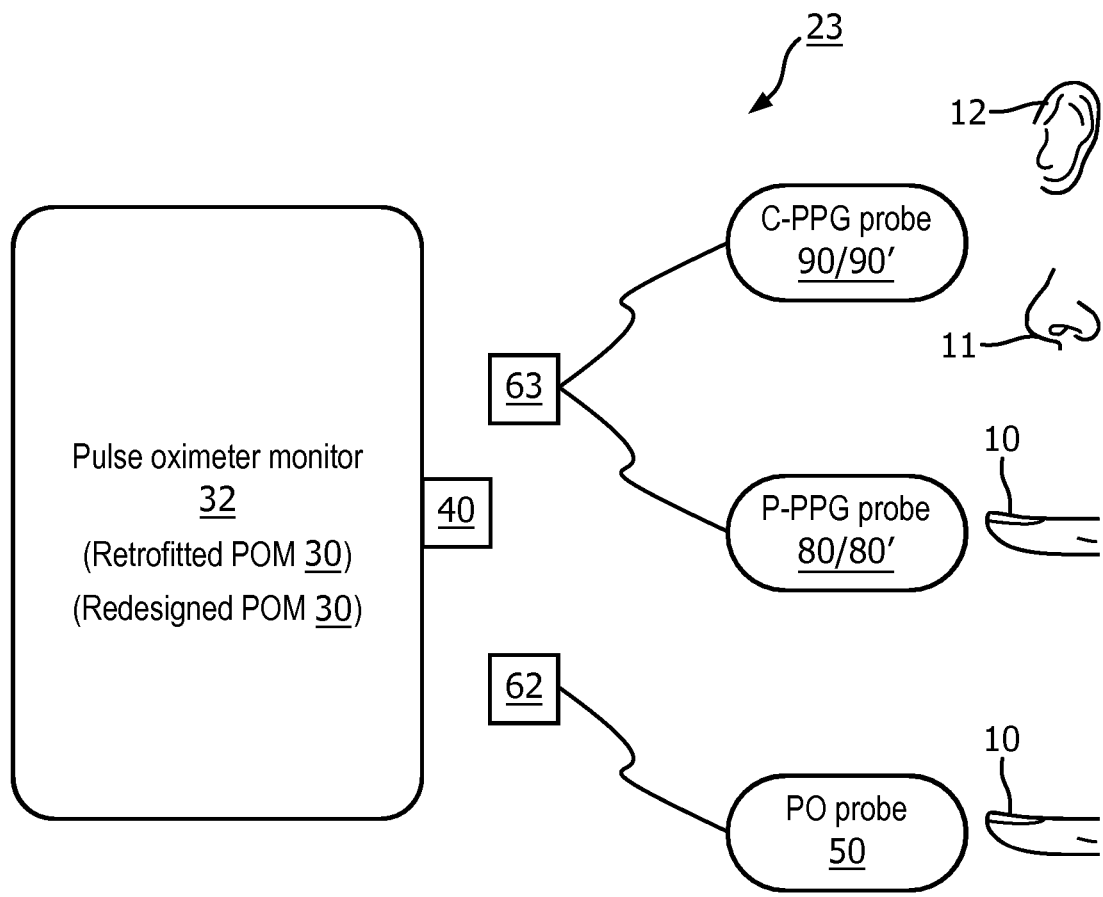
FIGS. 6A and 6B illustrates a third exemplary embodiment of PPG pulse oximeter in accordance with the inventive principles of the present disclosure.
Figure 6B:
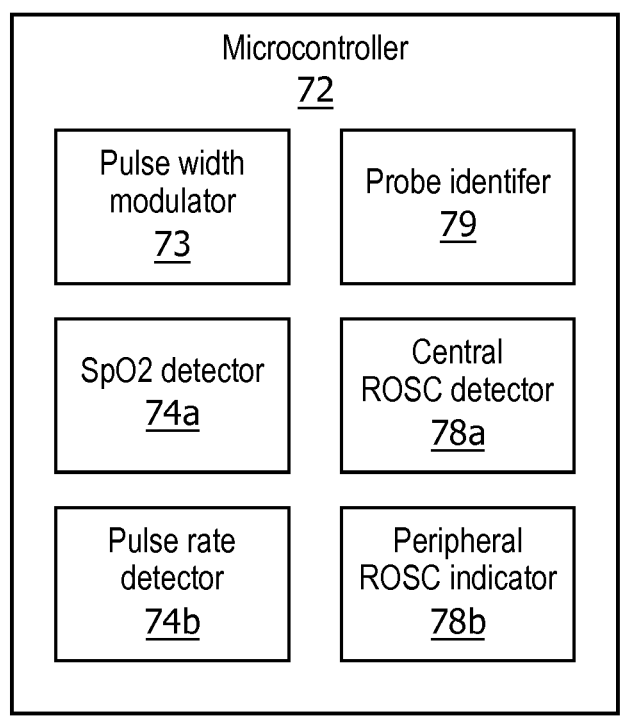

Referring to FIGS. 6A and 6B, a PPG pulse oximeter 23 of the present disclosure employs a pulse oximeter monitor 32, a dual PPG probe of FIGS. 4A and 4B or FIGS. 5A and 5B, and the pulse oximeter probe 50 of FIGS. 1A and 1B. To this end, information is encoded in a connector 62 of the pulse oximeter probe 50 and a connector 63 of the dual PPG probe via an identification means (e.g., via a coding resistor or an IC) whereby a probe identifier 79 of microcontroller 72 may ascertain whether a pulse oximetry probe or the dual PPG probe is attached to the pulse oximetry monitor 32. As such, a detection of the type of probe will determine which parts of the firmware will be activated. In case of a detection of a connection to dual PPG probe 80/90 or 80'/90' via connector 63, central ROSC detector 78*a* and peripheral ROSC detector 78*b* will be activated among other elements. Conversely, in case of a detection of connection to pulse oximetry probe 50 via connector 62, SpO2 detector 74*a* and pulse rate detector 74*b* will be activated among other elements. As a result, pulse oximeter monitor 32 will automatically switch to "CPR mode" upon connection with dual PPG probe 80/90 or 80'/90' and automatically switch to "SpO2 mode" upon connection with pulse oximetry probe 50.

Figure 7:
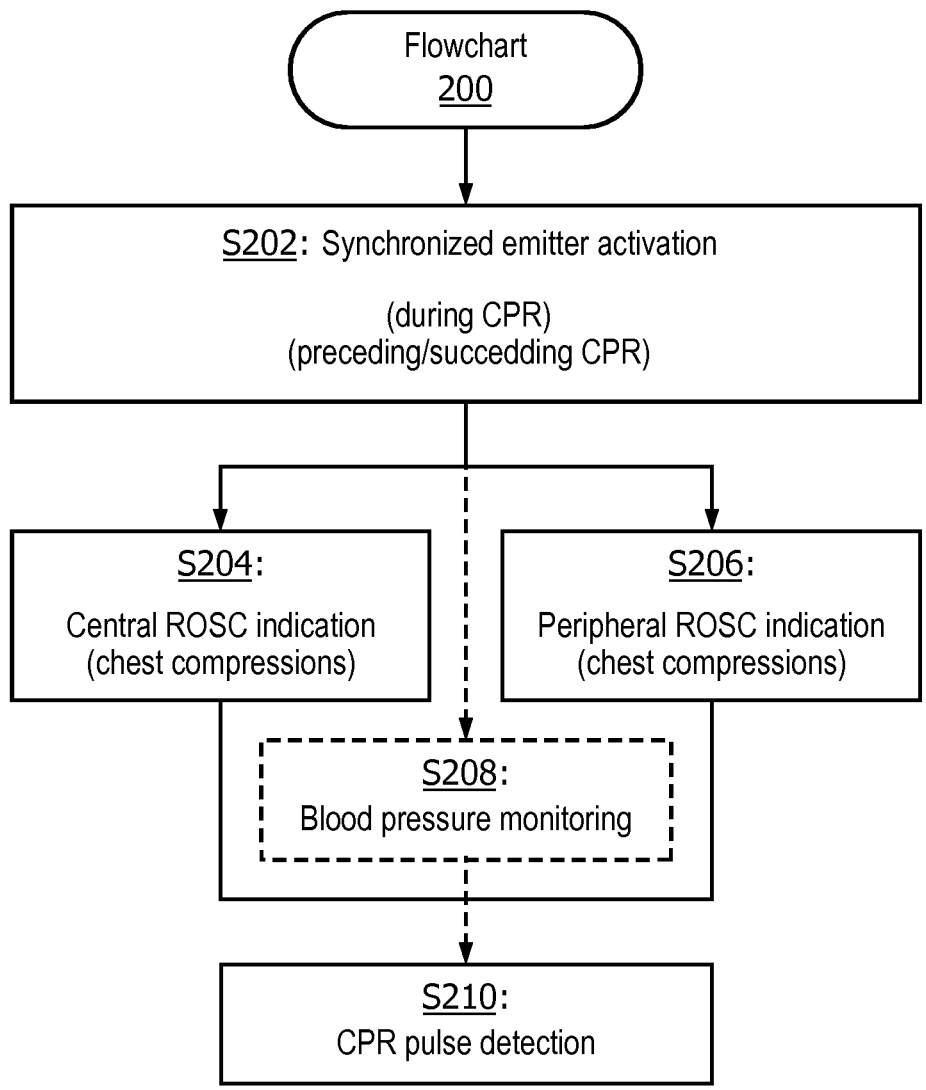
FIG. 7 illustrates a flowchart representative of an exemplary embodiment of a PPG pulse monitoring method in accordance with the inventive principles of the present disclosure.

FIG. 7 illustrates a flowchart 200 representing a PPG pulse monitoring method of the present disclosure. Referring to FIG. 7, a stage S202 of flowchart 200 encompasses a synchronized emitter activation during CPR, preceding CPR and/or succeeding CPR.

A stage S204 and a stage S206 of flowchart 200 encompasses an analysis of the PPG signals obtained from two (2) sites. Specifically, a central ROSC indicator 78*a* and a peripheral ROSC indicator 78*b* as previously described herein include algorithms designed to detect a spontaneous pulse component in the respective PPG signal during CPR, preceding CPR and/or succeeding CPR as known in the art of the present disclosure. Stage S204 and stage S206 may utilize additional information about the presence and rate of the chest compressions, derived from, e.g., an accelerometer, trans-thoracic impedance signal, a force signal, or a radar signal. The information about compressions can be used to determine how to analyze the PPG signals. First, a spectral analysis of the PPG signals taking into account all compression-related frequency components. Second, a filtering technique to remove or attenuate all compression-related frequency components from the PPG signals. Third, a technique which relies on a PPG signal acquired during a quiet period in CPR without any chest compression components.

Furthermore, an optional stage S208 of flowchart 200 may be applied to track blood pressure changes by analyzing time differences between the cardiac-induced pulses in the two synchronously acquired PPG signals, which can be implemented as a trend indicator for the status of the circulation. Stage S208 may be incorporated in a central ROSC indicator 78*a* or a peripheral ROSC indicator 78*b*.

A stage S210 of flowchart 200 provides for a display or communication of any pulse detection and/or circulation trend indication during CPR.

Once initially implemented, stage S204-S210 are continuously and simultaneously executed until an interruption or a termination of flowchart 200.

Referring to FIGS. 1-7, those having ordinary skill in the art will appreciate numerous benefits of the inventions of the present disclosure including, but not limited to, an improvement of pulse oximeters for pulse detection during, preceding and/or succeeding CPR.

The present disclosure disclosed herein has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Further, as one having ordinary skill in the art shall appreciate in view of the teachings provided herein, features, elements, components, etc. disclosed and described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and exemplary embodiments of the present disclosure, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar functionality, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of dual-PPG probes in combination with pulse oximeter monitors and operating methods thereof, (which embodiments are intended to be illustrative and not limiting), it is noted that modifications and variations can be made by persons having ordinary skill in the art in view of the teachings provided herein, including the appended Figures and claims. It is therefore to be understood that changes can be made in/to the preferred and exemplary embodiments of the present disclosure which are within the scope of the present disclosure and exemplary embodiments disclosed and described herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A PPG pulse oximeter, comprising:
a dual PPG probe including a circuit configuration of a central PPG sensor connected to a peripheral PPG sensor; and
a pulse oximeter monitor connectable to the circuit configuration of the central PPG sensor connected to the peripheral PPG sensor,
wherein, when the pulse oximeter monitor is connected to the circuit configuration of the central PPG sensor connected to the peripheral PPG sensor via a connector, the pulse oximeter monitor is configured to:
control synchronous generations of a central PPG signal by the central PPG sensor and of a peripheral PPG signal by the peripheral PPG sensor; and
control a CPR pulse detection by the dual PPG probe including a detection of a presence of a spontaneous pulse of the central PPG signal and a detection of a presence of a spontaneous pulse of the peripheral PPG signal.

2. The PPG pulse oximeter of claim 1,
wherein the central PPG sensor-includes a central light emitter optically coupled to a central light detector;
wherein the peripheral PPG sensor includes a peripheral light emitter optically coupled to a peripheral light detector;
wherein the central light emitter and the peripheral light emitter are connectable to the pulse oximeter monitor in an anti-parallel configuration; and
wherein the central light detector and the peripheral light detector are connectable to the pulse oximeter monitor is a parallel configuration.

3. The PPG pulse oximeter of claim 1,
wherein the central PPG sensor includes a central light emitter;
wherein the peripheral PPG sensor includes a peripheral light emitter;
wherein the central light emitter and the peripheral light emitter are connected to the pulse oximeter monitor in an anti-parallel configuration; and
wherein the dual PPG probe further includes a common photodetector optically coupled to the central light emitter and the peripheral light emitter.

4. The PPG pulse oximeter of claim 1, wherein the PPG pulse monitor is further configured in connection with the dual PPG probe to:
during chest compressions of a CPR, detect the presence of the spontaneous pulse of the central PPG signal and detect the presence of the spontaneous pulse of the peripheral PPG signal.

5. The PPG pulse oximeter of claim 1, wherein the PPG pulse monitor is further configured in connection with the dual PPG probe to:
at least one of preceding and succeeding chest compressions of a CPR, detect the presence of the spontaneous pulse of the central PPG signal and detect the presence of the spontaneous pulse of the peripheral PPG signal.

6. The PPG pulse oximeter of claim 1, wherein the PPG pulse monitor is further configured in connection with the dual PPG probe to:
measure a differential transit time between a cardiac-induced pulse of the central PPG signal and a cardiac-induced pulse of the peripheral PPG signal.

7. The PPG pulse oximeter of claim 1,
wherein the dual PPG probe further includes a sensor identification; and
wherein the pulse oximeter monitor is further configured in connection with the dual PPG probe to:
identify the connection of the dual PPG probe to the pulse oximeter monitor based on the sensor identification of the dual PPG probe.

8. The PPG pulse oximeter of claim 7, further comprising a pulse oximeter probe including a sensor identification; and
wherein the pulse oximeter monitor is further configured in connection with the pulse oximeter probe to:
identify the connection of the pulse oximeter probe to the pulse oximeter monitor based on the sensor identification of the pulse oximeter probe.

9. A PPG pulse monitoring method, comprising:
identifying, by a pulse oximeter monitor, a connection of the pulse oximeter monitor to a dual PPG probe including a circuit configuration of a central PPG sensor connected to a peripheral PPG sensor via a connector;
controlling, by the pulse oximeter monitor, synchronous generations of a central PPG signal by the central PPG sensor and of the peripheral PPG signal by the peripheral PPG sensor; and
controlling, by the pulse oximeter monitor, a CPR pulse detection by the dual PPG probe including detecting a presence of a spontaneous pulse of the central PPG signal and detecting a presence of a spontaneous pulse of the peripheral PPG signal.

10. The PPG pulse monitoring method of claim 9,
wherein the central PPG sensor includes a central light emitter optically coupled to a central light detector;
wherein the peripheral PPG sensor includes a peripheral light emitter optically coupled to a peripheral light detector;
wherein the central light emitter and the peripheral light emitter are connected to the pulse oximeter monitor in an anti-parallel configuration; and
wherein the controlling, by the pulse oximeter monitor, synchronous generations of a central PPG signal by the central PPG sensor and of the peripheral PPG signal by the peripheral PPG sensor includes:
controlling, by a sensor driver, synchronized activations of the central light emitter and the peripheral light emitter.

11. The PPG pulse monitoring method of claim 9,
wherein the central PPG sensor includes a central light emitter;
wherein the peripheral PPG sensor includes a peripheral light emitter;
wherein the central light emitter and the peripheral light emitter are connected to the pulse oximeter monitor in an anti-parallel configuration;
wherein the dual PPG probe further includes a common photodetector optically coupled to the central light emitter and the peripheral light emitter; and
wherein the controlling, by the pulse oximeter monitor, synchronous generations of a central PPG signal by the central PPG sensor and of the peripheral PPG signal by the peripheral PPG sensor includes:
controlling, by a sensor driver, synchronized activations of the central light emitter and the peripheral light emitter.

12. The PPG pulse monitoring method of claim 9, wherein both the detecting by pulse oximeter monitor of the presence of the spontaneous pulse of the central PPG signal and of the presence of the spontaneous pulse of the peripheral PPG signal are during chest compressions of a CPR.

13. The PPG pulse monitoring method of claim 9, wherein both the detecting by pulse oximeter monitor of the presence of the spontaneous pulse of the central PPG signal and of the presence of the spontaneous pulse of the peripheral PPG signal are at least one of preceding and succeeding chest compressions of a CPR.

14. The PPG pulse monitoring method of claim 9, wherein the controlling, by the pulse oximeter monitor further includes:
   measuring, by the pulse oximeter monitor, a differential transit time between a cardiac-induced pulse of the central PPG signal and a cardiac-induced pulse of the peripheral PPG signal.

15. The PPG pulse monitoring method of claim 9, further comprising:
   identifying, by the pulse oximeter monitor, a disconnection of the dual PPG probe from the pulse oximeter monitor and a subsequent connection of a pulse oximeter probe to the pulse oximeter monitor or a disconnection of a pulse oximeter probe from the pulse oximeter monitor and a subsequent connection of the dual PPG probe to the pulse oximeter monitor.

\* \* \* \* \*